(12) United States Patent
Xu et al.

(10) Patent No.: US 11,788,961 B2
(45) Date of Patent: Oct. 17, 2023

(54) METHOD FOR COATING A CELL CULTURE SURFACE (71) Applicant: TERUMO KABUSHIKI KAISHA, Tokyo (JP)

(72) Inventors: Zhe Xu, Kanagawa (JP); Takao Anzai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 301 days.

(21) Appl. No.: 17/020,511

(22) Filed: Sep. 14, 2020

(65) Prior Publication Data

US 2021/0270739 A1    Sep. 2, 2021

(30) Foreign Application Priority Data

Sep. 20, 2019 (JP) ................. 2019-172049

(51) Int. Cl.
| | |
|---|---|
| *G01N 21/64* | (2006.01) |
| *G01N 33/58* | (2006.01) |
| *G01N 33/68* | (2006.01) |
| *G01N 21/78* | (2006.01) |
| *G01N 33/00* | (2006.01) |
| *C12M 1/00* | (2006.01) |
| *C12M 1/12* | (2006.01) |

(52) U.S. Cl.
CPC ......... *G01N 21/6428* (2013.01); *C12M 23/20* (2013.01); *C12M 25/02* (2013.01); *C12M 25/10* (2013.01); *G01N 21/78* (2013.01); *G01N 33/582* (2013.01); *G01N 33/68* (2013.01); *G01N 2021/6439* (2013.01); *G01N 2033/0096* (2013.01)

(58) Field of Classification Search
CPC .............. G01N 21/6428; G01N 21/78; G01N 33/582; G01N 33/68; G01N 2021/6439; G01N 2033/0096; G01N 2021/6434; G01N 33/54306; G01N 2021/7786; C12M 23/20; C12M 25/02; C12M 25/10
See application file for complete search history.

(56) References Cited

U.S. PATENT DOCUMENTS

| | | | | |
|---|---|---|---|---|
| 2011/0294142 | A1* | 12/2011 | Lahiri ................. | C12N 5/0068 435/7.2 |
| 2013/0034869 | A1* | 2/2013 | Whitesides ....... | B01L 3/502738 435/7.92 |
| 2020/0147567 | A1* | 5/2020 | Hong ..................... | G01N 33/68 |

FOREIGN PATENT DOCUMENTS

| | | | | |
|---|---|---|---|---|
| WO | WO-9707389 A1 * | 2/1997 | ....... | G01N 33/54306 |
| WO | 2016-183350 A1 | 11/2016 | | |

\* cited by examiner

*Primary Examiner* — Samuel P Siefke
*Assistant Examiner* — Henry H Nguyen
(74) *Attorney, Agent, or Firm* — Sheridan Ross P.C.

(57) ABSTRACT

The present invention is to provide a method capable of visualizing a coating state of a protein adsorbent even on a substrate having a complicated structure, in particular, for use on a surface of an apparatus for culturing or growing living cells. The method comprises coating a series of substrates with selected protein adsorbents and fluorescent dye, irradiating selected coated substrates and determining a coating state from color development of the substrates.

15 Claims, 1 Drawing Sheet

METHOD FOR COATING A CELL CULTURE SURFACE

TECHNICAL FIELD

The present invention relates to a method of evaluating a coating state of a protein adsorbent or an adsorption state of a protein.

BACKGROUND

A cell culture technology has been recently used in a regenerative medicine or development of a new drug. In particular, the use of stem cells has been spotlighted, and a technology for repairing and replacing damaged or defective tissues by using stem cells expanded from donor cells has been actively studied. Most cells of an animal including human are adherent (anchorage-dependent) cells that cannot survive in a suspended state and survive in a state of adhering to something. Therefore, the adherent (anchorage-dependent) cells are cultured at a high density to obtain a cultured tissue similar to a living tissue. For the above purpose, a cell culture substrate has been coated with a protein adsorbent (cell adhesion factor) such as fibronectin, collagen, laminin, or the like.

Meanwhile, a structure of the cell culture substrate (cell culture container) has been diversified into a hollow fiber structure and the like, in addition to a conventional flat plate structure (for example, Patent Literature 1).

CITATION LIST

Patent Literatures

PTL 1: Patent Literature 1: JP 2018-519800 A

SUMMARY OF THE INVENTION

For such a culture container having a diversified and complicated structure, it is difficult or impossible to confirm whether a desired protein adsorbent is uniformly coated on the cell culture substrate by a nondestructive test.

Therefore, the present invention has been made in view of the above circumstances, and an object of the present invention is to provide a method capable of visualizing a coating state of a protein adsorbent even on a substrate having a complicated structure.

The present inventors have conducted intensive studies in order to solve the above problems. As a result, the present inventors have found that the above problems can be solved by appropriately combining a fluorescent dye, a protein adsorbent, and a protein detection reagent, thereby completing the present invention.

That is, the object can be achieved by a method of evaluating a coating state of a protein adsorbent or an adsorption state of a protein, the method including: preparing a substrate 1 in which a coating layer containing a protein adsorbent and a fluorescent dye is formed on at least one surface of a polymer substrate, and detecting a color development state 1 of the substrate 1 by irradiating the substrate 1 with light; preparing a substrate 2 in which a coating layer containing a protein adsorbent and a fluorescent dye and a coating layer containing a protein detection reagent are sequentially formed on at least one surface of a polymer substrate, and detecting a color development state 2 of the substrate 2 by irradiating the substrate 2 with light; preparing a substrate 3 in which a coating layer containing a protein adsorbent and a fluorescent dye is formed on at least one surface of a polymer substrate, obtaining a substrate 4 by introducing a sample containing a protein into the substrate 3, and detecting a color development state 3 of the substrate 4 by irradiating the substrate 4 with light; preparing a substrate 5 in which a coating layer containing a protein adsorbent and a fluorescent dye is formed on at least one surface of a polymer substrate, obtaining a substrate 6 by introducing a sample containing a protein into the substrate 5, obtaining a substrate 7 by introducing a protein detection reagent into the substrate 6, and detecting a color development state 4 of the substrate 7 by irradiating the substrate 7 with light; and evaluating a coating state of the protein adsorbent or an adsorption state of the protein by comparing the color development state 4 with the color development state 1, 2, or 3.

DETAILED DESCRIPTION

Hereinafter, embodiments of the present invention will be described with reference to the drawings as appropriate. It should be noted that the present invention is not limited to only the following embodiments. In addition, each drawing is expressed in an exaggerated manner for the convenience of description, and dimension ratios of components in each drawing may be different from actual ratios. In addition, in a case where the embodiments of the present invention are described with reference to the drawings, the same components are denoted by the same reference numerals in the description of the drawing, and redundant description is omitted.

In the present specification, "X to Y" indicating a range includes X and Y, and means "X or more and Y or less". In addition, unless otherwise specified, an operation and a measurement of physical properties and the like are carried out under conditions of room temperature (20 to 25° C.)/relative humidity of 40 to 50% RH.

The present invention relates to a method for evaluating a coating state of a protein adsorbent or an adsorption state of a protein that includes:

(1) providing a substrate 1 having a coating layer containing a protein adsorbent and a fluorescent dye formed on at least one surface of a polymer substrate, and irradiating the substrate 1 with light to observe a color development state 1 of the substrate 1 (step (1));

(2) providing a substrate 2 having a coating layer containing a protein adsorbent and a fluorescent dye and a coating layer containing a protein detection reagent sequentially formed on at least one surface of a polymer substrate, and irradiating the substrate 2 with light to observe a color development state 2 of the substrate 2 (step (2));

(3) providing a substrate 3 having a coating layer containing a protein adsorbent and a fluorescent dye formed on at least one surface of a polymer substrate, introducing a sample containing a protein onto the substrate 3 to obtain a substrate 4, and irradiating the substrate 4 with light to observe a color development state 3 of the substrate 4 (step (3));

(4) providing a substrate 5 having a coating layer containing a protein adsorbent and a fluorescent dye formed on at least one surface of a polymer substrate, introducing a sample containing a protein onto the substrate 5 to obtain a substrate 6, introducing a protein detection reagent onto the substrate 6 to obtain a substrate 7, and irradiating the substrate 7 with light to observe a color development state 4 of the substrate 7 (step (4)); and (5) comparing the color development state 4 with the color development state 1, 2, or 3 to evaluate a coating state of the protein adsorbent or an adsorption state of the protein (step (5)). According to the configuration, a coating state of a protein adsorbent or an adsorption state of a protein can be easily and visually observed. In addition, the coating state of the protein adsorbent or the adsorption state of the protein can be evaluated by a nondestructive test even on a substrate having a complicated structure. Here, a mechanism exhibiting the operation effects by the configuration of the present invention is presumed as follows. It should be noted that the present invention is not limited to the following presumption.

Figure 1:
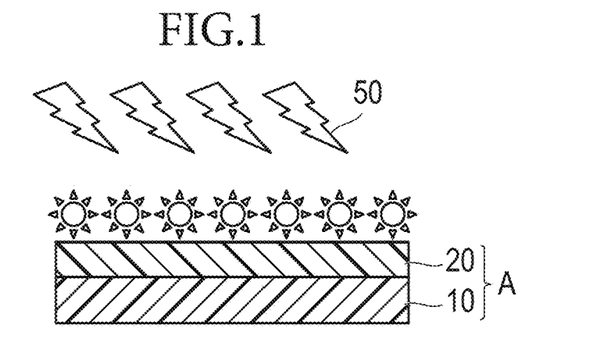
FIG. 1 is a view of a substrate in which a coating layer containing a protein adsorbent and a fluorescent dye is formed on a polymer substrate illustrating a method of the present invention.
Figure 3:
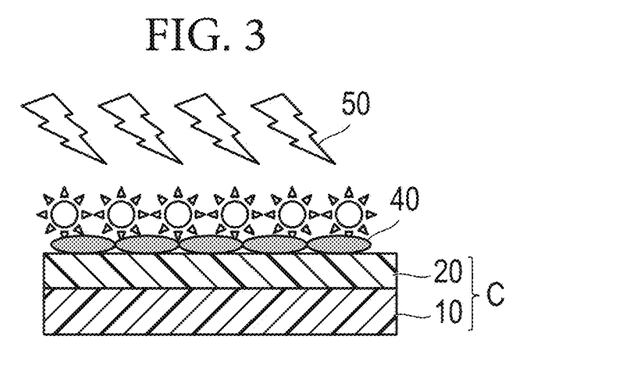
FIG. 3 is a view of a substrate C in which a coating layer containing a protein adsorbent and a fluorescent dye is formed on a polymer substrate.
Figure 4:
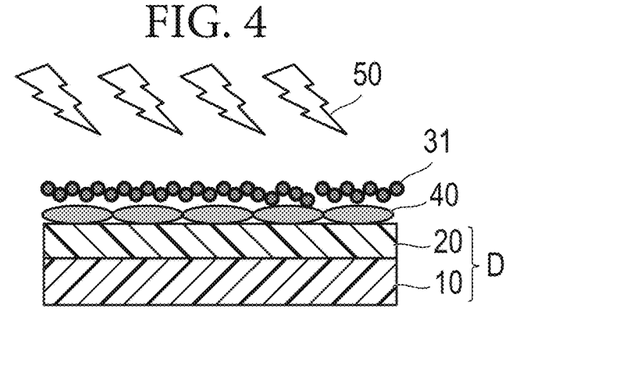
FIG. 4 is a view of a substrate in which a coating layer containing a protein adsorbent and a fluorescent dye is formed on a polymer substrate.

The mechanism exhibiting the operation effects by the configuration of the present invention will be described. In FIG. 1, a substrate A in which a coating layer 20 containing a protein adsorbent and a fluorescent dye is formed on a polymer substrate 10 (a substrate 1 according to the present invention) is provided. When the substrate A (substrate 1) is irradiated with light 50 of a specific wavelength for inducing the fluorescent dye in an excited state (hereinafter, simply referred to as "light 50"), the fluorescent dye in the coating layer is excited by the light 50 and emits intensive light when the fluorescent dye returns to a ground state from the excited state (a color development state 1 according to the present invention). In FIG. 22, a substrate B in which a coating layer 20 containing a protein adsorbent and a fluorescent dye and a coating layer 30 containing a protein detection reagent 31 are sequentially formed on a polymer substrate 10 (a substrate 2 according to the present invention) is provided. When the substrate B (substrate 2) is irradiated with light 50, the protein detection reagent 31 absorbs a part of the light 50. As a result, intensity of the light 50 reaching the fluorescent dye in the coating layer is reduced, and emission intensity of the fluorescent dye excited by the light 50 is reduced (a color development state 2 according to the present invention). Therefore, fluorescence intensity in the color development state 2 is weaker than that in the color development state 1 (fluorescence intensity: color development state 2<color development state 1). In FIG. 3, a substrate C in which a coating layer 20 containing a protein adsorbent and a fluorescent dye is formed on a polymer substrate 10 (a substrate 3 according to the present invention) is provided. A sample containing a protein 40 is added (introduced) onto the substrate C (a substrate 4 according to the present invention). Thereafter, when the substrate 4 is irradiated with light 50, the protein 40 absorbs a part of the light 50. Here, a degree of light absorption of the protein detection reagent 31 is larger than that of the protein 40. As a result, intensity of the light 50 reaching the fluorescent dye in the coating layer in FIG. 3 is lower than that in the case of FIG. 1 (the color development state 1), but is higher than that in the case of FIG. 2 (the color development state 2). That is, fluorescence intensity emitted from the fluorescent dye excited by the light 50 (a color development state 3) is lower than that in the case of FIG. 1 (the color development state 1), but is higher than that in the case of FIG. 2 (the color development state 2) (fluorescence intensity: color development state 2<color development state 3<color development state 1). In FIG. 4, a substrate D in which a coating layer 20 containing a protein adsorbent and a fluorescent dye is formed on a polymer substrate 10 (a substrate 5 according to the present invention) is provided. A sample containing a protein 40 is added (introduced) onto the substrate D (a substrate 6 according to the present invention). Then, the protein is adsorbed to the protein adsorbent in the coating layer 20. Next, a protein detection reagent 31 is introduced onto the substrate 6 (a substrate 7 according to the present invention). Then, the protein detection reagent 31 is conjugated to the protein 40 (a protein adsorbent-protein-protein detection reagent-conjugate). Next, when the substrate is irradiated with light 50, the conjugate strongly absorbs the light. As a result, the light 50 hardly reaches the fluorescent dye in the coating layer. That is, emission intensity of the fluorescent dye excited by the light 50 is significantly reduced (a color development state 4 according to the present invention). Therefore, fluorescence intensity in the color development state 4 is weaker than that in the color development state 2 (and those in the color development states 3, 1) (fluorescence intensity: color development state 4<color development state 2<color development state 3<color development state 1). Therefore, an adsorption state of a protein can be evaluated by comparing the color development state 4 with the color emission intensity 1, 2, or 3. In addition, a location at which the adsorption of the protein is observed corresponds to a location at which the protein adsorbent is present. Therefore, a coating state of a protein adsorbent can be evaluated by comparing the color development state 4 with the color emission intensity 1, 2, or 3. Furthermore, the color development state 4 is compared with the color development state 1 or 3 by adding the protein and the protein detection reagent on the substrate and then irradiating the substrate with light, but the operation(s) can be performed without depending on a shape of the substrate. Furthermore, the comparison can be performed by a nondestructive test. Therefore, according to the method, the coating state of the protein adsorbent or the adsorption state of the protein can be visualized even on a substrate having a complicated structure.

Step (1)

In the present step, the substrate 1 in which the coating layer containing the protein adsorbent and the fluorescent dye is formed on at least one surface of the polymer substrate is provided, and the color development state 1 of the substrate 1 is detected by irradiating the substrate 1 with light. As used herein, the "coating layer containing a protein adsorbent and a fluorescent dye" in the present step (1) is simply referred to as a "coating layer 1".

The polymer substrate is not particularly limited, and a substrate required for evaluation of a coating state of a protein adsorbent or an adsorption state of a protein can be used. Specifically, examples of a material constituting the polymer substrate can include, but are not limited to, a hydrophobic polymer such as polyamide (PA), polyaramid (PAA), polyether sulfone (PES), polyaryl ether sulfone (PAES), polysulfone (PSU), polyaryl sulfone (PASU), polycarbonate (PC), polyether, polyurethane (PUR), polyetherimide, polypropylene, polyethylene, polystyrene, polyacrylonitrile, polytetrafluoroethylene, or the like; a hydrophilic polymer such as polyvinylpyrrolidone (PVP), polyethylene glycol (PEG), polyglycolmonoester, a water-soluble cellulose derivative, polysorbate, a polyethylene-polypropylene oxide copolymer, or the like; and the like. The hydrophobic polymers may be used alone or in combination of two or more thereof. The hydrophilic polymers may be used alone or in combination of two or more thereof.

In one embodiment of the present invention, the polymer substrate preferably contains at least one selected from the group consisting of polyamide (PA), polyether sulfone (PES), polyaryl ether sulfone (PAES), and polyvinylpyrrolidone (PVP). Such a polymer substrate is preferably used as a hollow fiber membrane of a bioreactor.

The polymer substrate according to the present invention may be formed of a mixture of the hydrophobic polymer and the hydrophilic polymer, and for example, may be formed of a mixture (PAES/PVP/PA) of polyamide (PA), polyaryl ether sulfone (PAES), and polyvinylpyrrolidone (PVP). Such a polymer substrate is particularly preferably used as a hollow fiber membrane of a bioreactor. In a case where the polymer substrate is formed of the mixture of the hydrophobic polymer and the hydrophilic polymer, for example, a content of the hydrophobic polymer may be 65 to 95 wt %, and a content of the hydrophilic polymer may be 5 to 35 wt %, with respect to a total amount of the hydrophobic polymer and the hydrophilic polymer.

The polymer substrate has various structures (shapes) such as, but not limited to, a planar structure, a structure into which a porous body is inserted, a hollow fiber structure, a porous membrane structure, a sponge structure, a cotton-like (glass wool) structure, and the like. For example, for the purpose of a hollow fiber type bioreactor, it is preferable that the polymer substrate is a porous membrane (hollow fiber membrane) having a hollow fiber and composed of a plurality of hollow fibers.

In a preferred embodiment, an inner diameter (diameter) of the hollow fiber is not particularly limited, but is preferably 50 to 1,000 more preferably 100 µm to 500 µm, and particularly preferably about 150 µm to 350 µm. An outer diameter (diameter) of the hollow fiber is not particularly limited, but is preferably 100 µm to 1,200 µm, more preferably 150 µm to 700 µm, and particularly preferably about 200 µm to 500 Tim. A length of the hollow fiber is not particularly limited, but is preferably 50 mm to 900 mm, more preferably 100 mm to 700 mm, and particularly preferably about 150 mm to 500 mm. The number of hollow fibers constituting the hollow fiber membrane is not particularly limited, but is preferably about 1,000 to 100,000, more preferably 3,000 to 50,000, and particularly preferably about 5,000 to 25,000. In one embodiment, the polymer substrate is composed of about 9,000 hollow fibers with an average length of about 295 mm, an average inner diameter of 215 µm, and an average outer diameter of 315 µm.

An outer layer of the hollow fiber may have an opening structure having a uniform surface roughness. An opening (diameter) of a pore is not particularly limited, but is in the range of about 0.5 µm to about 3 µm. The number of holes in an outer surface of the hollow fiber may be in the range of about 10,000 to about 150,000 per square millimeter (1 $mm^2$). A thickness of the outer layer of the hollow fiber is not particularly limited, but, for example, is in the range of about 1 µm to about 10 µm. The hollow fiber may have an additional layer (second layer) formed on an outer side thereof. In this case, the additional layer (second layer) preferably has a sponge structure with a thickness of about 1 µm to about 15 µm. The second layer having such a structure can serve as a support of the outer layer. In addition, in the present embodiment, the hollow fiber may further have a subsequent layer (third layer) formed on an outer side of the second layer. In this case, the subsequent layer (third layer) preferably has a finger-like structure. When the third layer has such a structure, mechanical stability can be attained. In addition, a high void volume which makes a transfer resistance of molecules in the membrane low can be provided. In the present embodiment, during use, the finger-like void is filled with fluid, and a resistance for diffusion and convection is reduced by the fluid as compared with the case of a matrix having a sponge-filled structure having a low void volume. The third layer preferably has a thickness of about 20 µm to about 60 µm.

A method of producing a hollow fiber and a porous membrane is not particularly limited, and a known production method can be applied as it is or after appropriate modification. For example, it is preferable that fine pores are formed in a wall of the hollow fiber by a drawing method or a solid-liquid phase separation method.

A hollow fiber membrane used in a bioreactor is generally subjected to hydrophilic treatment in order to perform a medium replacement inside and outside the hollow fiber membrane. In one embodiment of the present invention, the polymer substrate is a hydrophilic polymer substrate.

Examples of a method of producing a hydrophilic polymer substrate can include, but are not particularly limited to, a method of producing a polymer substrate by a method known in the related art by using the hydrophilic polymer or the mixture of the hydrophobic polymer and the hydrophilic polymer, a method which comprises producing a polymer substrate by a method known in the related art by using the hydrophobic polymer or the mixture of the hydrophobic polymer and the hydrophilic polymer and then hydrophilizing a surface of the polymer substrate using known means such as plasma treatment, corona treatment, primer treatment, or the like, and the like.

As the material constituting the polymer substrate, a commercially available product may be used, and for example, a Polyflux (registered trademark) manufactured by Baxter, a Desmopan (registered trademark) manufactured by DIC Covestro Polymer Ltd., and the like may be used. Alternatively, for example, a cell culture/expansion system described in JP 2010-523118 A (JP 5524824 B2) (which corresponds to WO 2008/124229 A2), JP 2013-524854 A (JP 6039547 B2) (which corresponds to WO 2011/140231 A1), JP 2013-507143 A (JP 5819835 B2) (which corresponds to WO 2011/045644 A1), JP 2013-176377 A (which corresponds to WO 2008/109674 A2), JP 2015-526093 A (which corresponds to WO 2014/031666 A1), JP 2016-537001 A (which corresponds to WO 2015/073913 A1), JP 2016-536998 A (which corresponds to WO 2015/073918 A1), JP 2017-509344 A (which corresponds to WO 2015/148704 A1), JP 2018-519800 A (which corresponds to WO 2016/183350 A1), or the like, and further, a substrate used in a Quantum cell expansion system manufactured by TERUMO BCT, INC. may be used as the polymer substrate according to the present invention.

The coating layer containing the protein adsorbent and the fluorescent dye (coating layer 1) and the coating layer containing the protein detection reagent (coating layer 2) are formed on at least one surface of the polymer substrate to prepare the substrate 2.

The coating layer 1 may be formed on at least one surface required for evaluation of a coating state of a protein adsorbent or an adsorption state of a protein, but is preferably formed on only one surface. In addition, it is not necessary to form the coating layer on the entire surface of the polymer substrate, and the coating layer 1 is formed in at least a portion required for evaluation of a coating state of a protein adsorbent or an adsorption state of a protein. Preferably, the coating layer 1 is formed on the entire surface of the polymer substrate. For the purpose of a bioreactor, a coating layer containing a cell adhesion factor may be formed on the polymer substrate. In this case, the cell adhesion factor serves as a protein adsorbent. In such a case, the coating layer 1 may be formed by further coating a fluorescent dye on the coating layer containing the cell adhesion factor (protein adsorbent) (for details, see the following). To be specific, the coating layer 1 may have a form in which a layer containing a protein adsorbent and a layer containing a fluorescent dye are stacked, or a form in which a fluorescent dye is separately added to a layer containing a protein adsorbent.

The protein adsorbent used in the coating layer 1 is not particularly limited as long as it has protein adsorbability. For example, a cell adhesion factor such as fibronectin, collagen, laminin, or the like can be used. In addition, the protein adsorbent preferably has a structural unit represented by the following Formula (1), from the viewpoint of improved protein adsorbability. That is, in a preferred embodiment of the present invention, the protein adsorbent has a structural unit derived from furfuryl (meth)acrylate of the following Formula (1):

Chemical Formula 1

Formula (1)

in the Formula (1), $R^1$ is a hydrogen atom or a methyl group, and $R^2$ is a group represented by the following Formula (1-1) or the following Formula (1-2):

Chemical Formula 2

Formula (1-1)

Formula (1-2)

in the Formula (1-1) and the Formula (1-2), $R^3$ is an alkylene group having 1 to 3 carbon atoms.

In the present specification, the structural unit derived from furfuryl (meth)acrylate of the Formula (1) is simply referred to as a "furfuryl (meth)acrylate structural unit" or a "structural unit (1)".

In the present specification, the term "(meth)acrylate" includes both acrylate and methacrylate. Similarly, the term "(meth)acrylic acid" includes both acrylic acid and methacrylic acid, and the term "(meth)acryloyl" includes both acryloyl and methacryloyl.

In a preferred embodiment, the protein adsorbent has the structural unit derived from furfuryl (meth)acrylate of the Formula (1) (structural unit (1)). The structural unit derived from furfuryl (meth)acrylate of the Formula (1) (structural unit (1)) can impart protein adsorbability to the substrate. The structural units (1) may be used alone or in combination of two or more thereof. That is, the structural unit (1) may be composed of only one kind of the structural unit derived from furfuryl (meth)acrylate of the Formula (1), or may be composed of two or more kinds of the structural units derived from furfuryl (meth)acrylate of the Formula (1). A plurality of structural units (1) may be present in a block form or may be present in a random form.

In the Formula (1), $R^1$ is a hydrogen atom or a methyl group.

$R^2$ is a group represented by the Formula (1-1) or the Formula (1-2). Among them, $R^2$ is preferably a group represented by the Formula (1-1), from the viewpoint of further improved protein adsorbability or the like.

In the Formula (1-1) and the Formula (1-2), $R^3$ is an alkylene group of 1 to 3 carbon atoms. Here, examples of the alkylene group of 1 to 3 carbon atoms include a methylene group ($-CH_2-$), an ethylene group ($-CH_2CH_2-$), a trimethylene group ($-CH_2CH_2CH_2-$), and a propylene group ($-CH(CH_3)CH_2-$ or $-CH_2CH(CH_3)-$). Among them, $R^3$ is preferably a methylene group ($-CH_2-$) or an ethylene group ($-CH_2CH_2-$), and more preferably a methylene group ($-CH_2-$), from the viewpoint of further improved protein adsorbability or the like.

Specifically, examples of the furfuryl (meth)acrylate can include tetrahydrofurfuryl acrylate, 5-[2-(acryloyloxy)ethyl]tetrahydrofuran, 2-furylmethyl acrylate, 5-[2-(acryloyloxy)ethyl]furan, tetrahydrofurfuryl methacrylate, 5-[2-(methacryloyloxy)ethyl]tetrahydrofuran, 2-furylmethyl methacrylate, 5-[2-(methacryloyloxy)ethyl]furan, and the like. Among them, tetrahydrofurfuryl (meth)acrylate is preferable, and tetrahydrofurfuryl acrylate (THFA) is more preferable, from the viewpoint of further improved protein adsorbability or the like.

The protein adsorbent may be composed of only the structural unit derived from furfuryl (meth)acrylate of the Formula (1), or may have a structural unit derived from another monomer as well as the structural unit derived from furfuryl (meth)acrylate of the Formula (1). The another monomer is not particularly limited as long as it does not inhibit desired properties (protein adsorbability). Specifically, examples of the another monomer can include an ethylenically unsaturated monomer having a hydroxyl group, alkoxyalkyl (meth)acrylate, acrylamide, N,N-dimethylacrylamide, N,N-diethylacrylamide, methacrylamide, N,N-dimethylmethacrylamide, N,N-diethylmethacrylamide, ethylene, propylene, N-vinylacetamide, N-isopropenylacetamide, N-(meth)acryloylmorpholine, and the like. Among them, as the another monomer, an ethylenically unsaturated monomer having a hydroxyl group and alkoxyalkyl (meth)acrylate are preferable, from the viewpoint of further improved protein adsorbability. A composition of a structural unit derived from another monomer in a case where the protein adsorbent further has a structural unit derived from another monomer including an ethylenically unsaturated monomer having a hydroxyl group and alkoxyalkyl (meth)acrylate is not particularly limited as long as desired properties (protein adsorbability) are not inhibited, and is preferably more than 0 mol % and less than 10 mol %, and more preferably about 3 to 8 mol %, with respect to a total structural unit. That is, in a preferred embodiment, the protein adsorbent according to the present invention is composed only of a structural unit derived from furfuryl (meth)acrylate of the Formula (1) (preferred embodiment A), or has a structural unit derived from furfuryl (meth)acrylate of the Formula (1) and a structural unit derived from an ethylenically unsaturated monomer having a hydroxyl group (preferred embodiment B), or has a structural unit derived from furfuryl (meth)acrylate of the Formula (1) and a structural unit derived from alkoxyalkyl (meth)acrylate represented by the following Formula (3) (preferred embodiment C). Hereinafter, the preferred embodiments A, B, and C will be described.

Chemical Formula 3

Formula (3)

In the Formula (3), $R^6$ is a hydrogen atom or a methyl group; $R^7$ is an alkylene group having 2 to 3 carbon atoms; and $R^8$ is an alkyl group having 1 to 3 carbon atoms.

Preferred Embodiment A

In the preferred embodiment A, the protein adsorbent is composed of a homopolymer of tetrahydrofurfuryl acrylate, 5-[2-(acryloyloxy)ethyl]tetrahydrofuran, 2-furylmethyl acrylate, 5-[2-(acryloyloxy)ethyl]furan, tetrahydrofurfuryl methacrylate, 5-[2-(methacryloyloxy)ethyl]tetrahydrofuran, 2-furylmethyl methacrylate, or 5-[2-(methacryloyloxy) ethyl]furan, or a copolymer consisting of two or more thereof. Among them, the protein adsorbent is preferably composed of polytetrahydrofurfuryl acrylate (pTHFA) or polytetrahydrofurfuryl methacrylate, and more preferably composed of polytetrahydrofurfuryl acrylate (pTHFA), from the viewpoint of further improved protein adsorbability.

In the preferred embodiment A, a weight average molecular weight (Mw) of the protein adsorbent is not particularly limited, but is preferably in the range of 50,000 to 800,000. In the above range, solubility of the protein adsorbent in a solvent can be improved, and the protein adsorbent can be easily and uniformly applied to the substrate. The weight average molecular weight of the protein adsorbent is more preferably in the range of 100,000 to 500,000, and particularly preferably in the range of 150,000 to 350,000, from the viewpoint of improved coating film formability.

In the present specification, a value measured by gel permeation chromatography (GPC) using polystyrene as a standard substance and tetrahydrofuran (THF) as a mobile phase is adopted as the "weight average molecular weight (Mw)". Specifically, the protein adsorbent is dissolved in tetrahydrofuran (THF) so that a concentration thereof is 10 mg/ml, to prepare a sample. For the sample prepared as described above, a GPC column LF-804 (manufactured by Showa Denko K.K.) is attached to a GPC system LC-20 (manufactured by Shimadzu Corporation), THF is allowed to flow as a mobile phase, and polystyrene is used as a standard substance to measure GPC of the protein adsorbent. After preparing a calibration curve with a standard polystyrene, a weight average molecular weight (Mw) of the protein adsorbent is calculated based on this curve.

Preferred Embodiment B

In the preferred embodiment B, the protein adsorbent has a structural unit derived from furfuryl (meth)acrylate of the Formula (1) (structural unit (1)) and a structural unit derived from an ethylenically unsaturated monomer having a hydroxyl group (structural unit (2)). It is presumed that the furfuryl (meth)acrylate (structural unit (1)) imparts protein adsorbability to the substrate. It is also presumed that the hydroxyl group (—OH) contained in the structural unit (2) promotes protein adsorbability of the protein adsorbent to the surface of the substrate. It should be noted that the above description is merely presumption, and the present invention is not limited to the above description.

The structural unit (1) is as defined above. Therefore, the description thereof is omitted here.

The structural unit (2) is a structural unit derived from an ethylenically unsaturated monomer having a hydroxyl group. Here, the ethylenically unsaturated monomer having a hydroxyl group, which constitutes the structural unit (2), is not particularly limited as long as it is a compound having one or more hydroxyl groups (—OH) and one or more ethylenically unsaturated groups in one molecule. Here, the "ethylenically unsaturated group" refers to a group formed by substituting a hydrogen atom of ethylene ($CH_2$=$CH_2$), and examples thereof can include a (meth)acryloyl group, a vinyl group, an allyl group, a vinyl ether group, and the like. It should be noted that only one or two or more of these groups may be contained in one molecule of the ethylenically unsaturated monomer.

Among them, as the ethylenically unsaturated group, a (meth)acryloyl group ($CH_2$=CR—C(=O)—; R is a hydrogen atom or a methyl group) is preferable. That is, according to a preferred embodiment of the present invention, the ethylenically unsaturated monomer has a (meth)acryloyl group. Therefore, the ethylenically unsaturated monomer is preferably a compound having one or more hydroxyl groups and one or more acryloyl or methacryloyl groups in one molecule. An upper limit of the number of each of hydroxyl groups and (meth)acryloyl groups that are contained in the ethylenically unsaturated monomer is not particularly limited, but the number of hydroxyl groups in one molecule is preferably 3 or less, more preferably 2 or less, and particularly preferably 1, from the viewpoint of protein adsorbability. In addition, the number of (meth)acryloyl groups in one molecule is preferably 3 or less, and more preferably 2 or less, from the viewpoints of easiness of preparation of the protein adsorbent with furfuryl (meth)acrylate represented by the Formula (1), controllability of a composition (molar ratio) of each structural unit, and controllability of the protein adsorbability. In particular, the number of (meth)acryloyl groups in one molecule is particularly preferably 1, from the viewpoint that the composition (molar ratio) of each structural unit is controlled and protein adsorbability is thus further improved.

According to a preferred embodiment of the present embodiment, the structural unit (2) is derived from hydroxyalkyl (meth)acrylate represented by the following Formula (2). That is, it is preferable that the ethylenically unsaturated monomer is hydroxyalkyl (meth)acrylate represented by the following Formula (2). It should be noted that the structural units (2) constituting the protein adsorbent may be used alone or in combination of two or more thereof. That is, the structural unit (2) may be composed of only one kind of a structural unit derived from hydroxyalkyl (meth)acrylate represented by the following Formula (2), or may be composed of two or more kinds of structural units derived from hydroxyalkyl (meth)acrylate represented by the following Formula (2). It should be noted that a plurality of structural units (2) may be present in a block form or may be present in a random form.

Chemical Formula 4

Formula (2)

In the Formula (2), $R^4$ is a hydrogen atom or a methyl group. $R^5$ is an alkylene group having 2 to 3 carbon atoms. Here, examples of the alkylene group having 2 to 3 carbon atoms include an ethylene group (—$CH_2CH_2$—), a trimethylene group (—$CH_2CH_2CH_2$—), and a propylene group (—$CH(CH_3)CH_2$— or —$CH_2CH(CH_3)$—). Among them, $R^5$ is preferably an ethylene group (—$CH_2CH_2$—) or a trimethylene group (—$CH_2CH_2CH_2$—), and more preferably an ethylene group (—$CH_2CH_2$—), from the viewpoint of further improving protein adsorbability or the like.

That is, examples of the hydroxyalkyl (meth)acrylate include hydroxyethyl acrylate, hydroxypropyl acrylate, hydroxyisopropyl acrylate, hydroxyethyl methacrylate, hydroxypropyl methacrylate, hydroxyisopropyl methacrylate, and the like. These hydroxyalkyl (meth)acrylates may be used alone or in combination of two or more thereof. Among them, the hydroxyalkyl (meth)acrylate is preferably hydroxyethyl (meth)acrylate, and more preferably hydroxyethyl methacrylate (HEMA), from the viewpoint of further improving protein adsorbability or the like.

A composition of each of the structural unit (1) and the structural unit (2) is not particularly limited. The protein adsorbent preferably has more than 20 mol % and less than 100 mol % of the structural unit (1) derived from furfuryl (meth)acrylate represented by Formula (1) and more than 0 mol % and less than 80 mol % of the structural unit (2) derived from an ethylenically unsaturated monomer having a hydroxyl group, from the viewpoint of protein adsorbability. More preferably, the protein adsorbent has 35 mol % or more and 98 mol % or less of the structural unit (1) and 2 mol % or more and 65 mol % or less of the structural unit (2). Still more preferably, the protein adsorbent has 40 mol % or more and 95 mol % or less of the structural unit (1) and 5 mol % or more and 60 mol % or less of the structural unit (2). Even still more preferably, the protein adsorbent has 50 mol % or more and 93 mol % or less of the structural unit (1) and 7 mol % or more and 50 mol % or less of the structural unit (2). Particularly preferably, the protein adsorbent has 55 mol % or more and 90 mol % or less of the structural unit (1) and 10 mol % or more and 45 mol % or less of the structural unit (2). Most preferably, the protein adsorbent has 60 mol % or more and 90 mol % or less of the structural unit (1) and 10 mol % or more and 40 mol % or less of the structural unit (2). It should be noted that a total of the structural unit (1) and the structural unit (2) is 100 mol %. In a case where the structural unit (1) is composed of two or more kinds of structural units (1), a composition of the structural unit (1) is a ratio (molar ratio (mol %)) of a total of the structural units (1) to the total of the structural unit (1) and the structural unit (2). Similarly, in a case where the structural unit (2) is composed of two or more kinds of structural units (2) (particularly preferably, two or more kinds of the structural units derived from hydroxyalkyl (meth)acrylate represented by the Formula (2)), a composition of the structural unit (2) is a ratio (molar ratio (mol %)) of a total of the structural units (2) to the total of the structural unit (1) and the structural unit (2).

In the present preferred embodiment B, the protein adsorbent has the structural unit (1) and the structural unit (2), and if necessary, a structural unit derived from another monomer as described above. Here, an arrangement of each structural unit is not particularly limited, and may have a block form (block copolymer-type protein adsorbent), a random form (random copolymer-type protein adsorbent), or an alternating form (alternating copolymer-type protein adsorbent). In consideration of further improvement of protein adsorbability or the like, the protein adsorbent is preferably composed of only the structural unit (1) and the structural unit (2).

In the preferred embodiment B, a weight average molecular weight (Mw) of the protein adsorbent is not particularly limited, but is preferably in the range of 50,000 to 800,000. In the above range, solubility of the protein adsorbent in a solvent can be improved, and the protein adsorbent can be easily and uniformly applied to the substrate. The weight average molecular weight of the protein adsorbent is more preferably in the range of 100,000 to 500,000, and particularly preferably in the range of 150,000 to 350,000, from the viewpoint of improving coating film formability.

Embodiment C

In the preferred embodiment C, the protein adsorbent has the structural unit derived from furfuryl (meth)acrylate of the Formula (1) (structural unit (1)) and a structural unit derived from alkoxyalkyl (meth)acrylate represented by the following Formula (3) (structural unit (3)). It is presumed that the furfuryl (meth)acrylate (structural unit (1)) imparts protein adsorbability to the substrate. It is also presumed that the alkoxyalkyl (meth)acrylate (structural unit (3)) imparts protein adsorbability (further, antithrombotic property) to the substrate. It should be noted that the above description is merely presumption, and the present invention is not limited to the above description.

The structural unit (1) is as defined above. Therefore, the description thereof is omitted here.

The structural unit (3) is derived from alkoxyalkyl (meth) acrylate of the following Formula (3). It should be noted that the structural units (3) constituting the protein adsorbent may be used alone or in combination of two or more thereof. That is, the structural unit (3) may be composed of only one kind of a structural unit derived from alkoxyalkyl (meth) acrylate of the following Formula (3), or may be composed of two or more kinds of structural units derived from alkoxyalkyl (meth)acrylate of the following Formula (3). It should be noted that a plurality of structural units (3) may be present in a block form or may be present in a random form.

Chemical Formula 5

Formula (3)

In the Formula (3), $R^6$ is a hydrogen atom or a methyl group. $R^7$ is an alkylene group having 2 to 3 carbon atoms. Here, examples of the alkylene group having 2 to 3 carbon atoms include an ethylene group (—$CH_2CH_2$—), a trimethylene group (—$CH_2CH_2CH_2$—), and a propylene group (—$CH(CH_3)CH_2$— or —$CH_2CH(CH_3)$—). Among them, $R^7$ is preferably an ethylene group (—$CH_2CH_2$—) or a propylene group, and more preferably an ethylene group (—CH$_2$CH$_2$—), from the viewpoints of further improvement of protein adsorbability (further, antithrombotic property), an excellent balance between protein adsorbability and antithrombotic property, and the like. In addition, R$^8$ is an alkyl group having 1 to 3 carbon atoms. Here, examples of the alkyl group having 1 to 3 carbon atoms include a methyl group, an ethyl group, an n-propyl group, and an isopropyl group. Among them, R$^8$ is preferably a methyl group or an ethyl group, and more preferably a methyl group, from the viewpoints of further improvement of protein adsorbability (further, antithrombotic property), an excellent balance between protein adsorbability and antithrombotic property, and the like.

That is, examples of the alkoxyalkyl (meth)acrylate can include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, butoxyethyl methacrylate, and the like. Among them, methoxyethyl (meth) acrylate, ethoxyethyl (meth) acrylate, or methoxybutyl (meth)acrylate is preferable, methoxyethyl (meth) acrylate is more preferable, and methoxyethyl acrylate (MEA) is particularly preferable, from the viewpoint of further improving protein adsorbability or the like.

A composition of each of the structural unit (1) and the structural unit (3) is not particularly limited. The protein adsorbent preferably has 95 to 35 mol % of the structural unit (1) derived from furfuryl (meth)acrylate represented by the Formula (1) and 5 to mol % of the structural unit (3) derived from alkoxyalkyl (meth)acrylate represented by the Formula (3), from the viewpoint of protein adsorbability. More preferably, the protein adsorbent has 90 to 40 mol % of the structural unit (1) derived from furfuryl (meth)acrylate of the Formula (1) and 10 to 60 mol % of the structural unit (3) derived from alkoxyalkyl (meth)acrylate of the Formula (3). Still more preferably, the protein adsorbent has 70 to 40 mol % of the structural unit (1) derived from furfuryl (meth)acrylate of the Formula (1) and 30 to 60 mol % of the structural unit (3) derived from alkoxyalkyl (meth)acrylate of the Formula (3). Particularly preferably, the protein adsorbent has 60 to 40 mol % of the structural unit (1) derived from furfuryl (meth)acrylate of the Formula (1) and 40 to 60 mol % of the structural unit (3) derived from alkoxyalkyl (meth)acrylate of the Formula (3). The protein adsorbent having such a composition can exhibit further excellent balance between protein adsorbability and antithrombotic property. Therefore, a case in which a sample containing proteins is blood, it is particularly effective. It should be noted that a total of the structural unit (1) and the structural unit (3) is 100 mol %. In a case where the structural unit (1) is composed of two or more kinds of structural units (1), a composition of the structural unit (1) is a ratio (molar ratio (mol %)) of a total of the structural units (1) to the total of the structural unit (1) and the structural unit (3). Similarly, in a case where the structural unit (3) is composed of two or more kinds of structural units (3), a composition of the structural unit (3) is a ratio (molar ratio (mol %)) of a total of the structural units (3) to the total of the structural unit (1) and the structural unit (3).

In the present preferred embodiment C, the protein adsorbent has the structural unit (1) and the structural unit (3), and if necessary, a structural unit derived from another monomer as described above. Here, an arrangement of each structural unit is not particularly limited, and may have a block form (block copolymer-type protein adsorbent), a random form (random copolymer-type protein adsorbent), or an alternating form (alternating copolymer-type protein adsorbent). In consideration of further improvement of protein adsorbability, further appropriate balance between protein adsorbability and antithrombotic property, and the like, the protein adsorbent is preferably composed of only the structural unit (1) and the structural unit (3).

A weight average molecular weight (Mw) of the protein adsorbent according to the present invention is not particularly limited, but is preferably in the range of 50,000 to 1,000,000. In the above range, solubility of the protein adsorbent in a solvent can be improved, and the protein adsorbent can be easily and uniformly applied to the substrate. The weight average molecular weight of the protein adsorbent is more preferably in the range of 100,000 to 500,000, and particularly preferably in the range of 250,000 to 400,000, from the viewpoint of improving coating film formability.

The protein adsorbent according to the present invention can be produced by applying a polymerization method known in the related art such as bulk polymerization, suspension polymerization, emulsion polymerization, solution polymerization, a living radical polymerization method, a polymerization method using a macro-initiator, a polycondensation method, or the like, without particular limitation. Specifically, for example, in a case where the protein adsorbent according to the present invention is composed of a block copolymer, a living radical polymerization method or a polymerization method using a macro-initiator is preferably used. The living radical polymerization method is not particularly limited, and for example, a method described in JP H11-263819 A, JP 2002-145971 A, JP 2006-316169 A, or the like, an atom transfer radical polymerization (ATRP) method, and the like can be applied as it is or after appropriate modification.

Alternatively, for example, in a case where the protein adsorbent according to the present invention is composed of a random copolymer, it is preferable to use a (co)polymerization method which comprises stirring furfuryl (meth)acrylate of the Formula (1) (in the preferred embodiment A), and (in the preferred embodiment B) the ethylenically unsaturated monomer having the hydroxyl group (preferably, hydroxyalkyl (meth)acrylate of the Formula (2)) or (in the preferred embodiment C) the alkoxyalkyl (meth)acrylate of the Formula (3), and if necessary, one kind or two or more kinds of monomers copolymerizable therewith (another monomer, copolymerizable monomer) together with a polymerization initiator in a polymerization solvent to prepare a monomer solution, and heating the monomer solution. Hereinafter, "the furfuryl (meth)acrylate of the Formula (1), and (in the preferred embodiment B) the ethylenically unsaturated monomer having the hydroxyl group (preferably, hydroxyalkyl (meth)acrylate of the Formula (2)) or (in the preferred embodiment C) the alkoxyalkyl (meth)acrylate of the Formula (3), and if necessary, one kind or two or more kinds of monomers copolymerizable therewith (another monomer, copolymerizable monomer)" is referred to as a "monomer for polymerization". In the above method, the polymerization solvent that can be used in the preparation of the monomer solution is not particularly limited as long as it can dissolve the monomer(s) to be used. Examples thereof can include aqueous solvents such as water, alcohols such as methanol, ethanol, propanol, isopropanol, and the like, polyethylene glycols, and the like; aromatic-based solvents such as toluene, xylene, tetralin, and the like; halogen-based solvents such as chloroform, dichloroethane, chlorobenzene, dichlorobenzene, trichlorobenzene, and the like; and the like. Among them, in consideration of easy solubility of the monomer(s) or the like, methanol is preferable. In addition, a monomer concentration in the monomer solution is not particularly limited. The monomer concentration in the monomer solution is generally 1 to 60 wt %, more preferably 5 to 50 wt %, and particularly preferably 10 to 45 wt %. It should be noted that the monomer concentration refers to a total concentration of the monomer for polymerization.

The polymerization initiator is not particularly limited, and a known polymerization initiator may be used. A radical polymerization initiator is preferable in terms of excellent polymerization stability. Specific examples thereof can include persulfates such as potassium persulfate (KPS), sodium persulfate, ammonium persulfate, and the like; peroxides such as hydrogen peroxide, t-butyl peroxide, methyl ethyl ketone peroxide, and the like; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazolin-2-yl)propane]dihydrochloride, 2,2'-azobis[2-(2-imidazolin-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(secondary butyl) peroxydicarbonate, azobiscyanovaleric acid, and the like; and the like. In addition, for example, a reducing agent such as sodium sulfite, sodium hydrogen sulfite, ascorbic acid, or the like may be used in combination with the radical polymerization initiator as a redox-based initiator. A blending amount of the polymerization initiator is preferably 0.0005 to 0.005 moles with respect to 1 mole of a total amount of the monomer for polymerization. With such a blending amount of the polymerization initiator, the (co)polymerization of the monomer for polymerization can be more efficiently carried out.

The polymerization initiator may be mixed with the monomer for polymerization and the polymerization solvent as it is, or may be mixed with the monomer for polymerization in a solution state obtained by dissolving the monomer for polymerization in another solvent in advance and the polymerization solvent. In the latter case, the another solvent is not particularly limited as long as it can dissolve the polymerization initiator, and an example thereof can include the same solvent as the above polymerization solvent. In addition, the another solvent may be the same as or different from the above polymerization solvent, but is preferably a solvent that is the same as the above polymerization solvent in consideration of easy control of polymerization or the like. In addition, in this case, a concentration of the polymerization initiator in the another solvent is not particularly limited, but an amount of the polymerization initiator added is preferably 0.1 to 10 parts by weight, and more preferably 0.5 to 5 parts by weight, with respect to 100 parts by weight of the another solvent, in consideration of easy mixing or the like.

In a case of using the polymerization initiator in a solution state, a solution of the monomer for polymerization dissolved in the polymerization solvent may be subjected to deaeration treatment in advance before adding the polymerization initiator. For the deaeration treatment, for example, the solution may be bubbled with an inert gas such as nitrogen gas, argon gas, or the like for about 0.5 to 5 hours. During the deaeration treatment, a temperature of the solution may be adjusted to about 30° C. to 80° C., and preferably, may be adjusted to a polymerization temperature in the following polymerization step.

Next, the monomer is (co)polymerized by heating the monomer solution. Here, as a (co)polymerization method, for example, a known polymerization method such as radical polymerization, anionic polymerization, cationic polymerization or the like can be adopted, and preferably, radical polymerization by which production is easily performed is used.

A (co)polymerization condition is not particularly limited as long as it is a condition in which a desired monomer for polymerization can be (co)polymerized. Specifically, a (co)polymerization temperature is preferably 30 to 80° C. and more preferably 40° C. to 55° C. In addition, a (co)polymerization time is preferably 1 to 24 hours, and preferably 5 to 12 hours. Under such a condition, (co)polymerization of each monomer can be more efficiently carried out. In addition, it is possible to effectively suppress or prevent gelation in the (co)polymerization step and to achieve high production efficiency.

In addition, during the polymerization, a chain transfer agent, a polymerization rate modifier, a surfactant, and other additives may be appropriately used, if necessary.

An atmosphere in which a (co)polymerization reaction is carried out is not particularly limited, and the reaction can be carried out in an air atmosphere, an inert gas atmosphere such as of nitrogen gas, argon gas, or the like, or the like. In addition, during the (co)polymerization reaction, a reaction solution may be stirred.

A (co)polymer after the (co)polymerization can be purified by a general purification method such as a reprecipitation method (precipitation method), a dialysis method, an ultrafiltration method, an extraction method, or the like.

The (co)polymer after the purification can be dried by any method such as freeze drying, reduced pressure drying, spray drying, heat drying, or the like, but freeze drying or reduced pressure drying is preferable from the viewpoint that an influence on physical properties of the polymer is small.

The fluorescent dye used in the coating layer 1 is not particularly limited as long as it is excited when being irradiated with light such as ultraviolet rays or the like and emits inherent fluorescence. The fluorescent dye is preferably a xanthene-based dye from the viewpoint of visibility or the like. Specifically, examples of the xanthene-based dye can include, but are not limited to, coumarin, cyanine, benzofuran, quinoline, quinazolinone, indole, benzazole, borapolyazaindacene, fluorescein, rhodamine, rhodool, and the like. In addition, a fluorescent dye having a polymerizable group such as a (meth)acrylic group or the like is preferably used from the viewpoint of film strength of the coating layer 1, dye elution suppression effect, adhesion to the polymer substrate, or the like. Here, the fluorescent dye may be synthesized or a commercially available product may be used. Examples of the commercially available product can include a xanthene-based dye such as R13 (color: fluorescent purple, polymerizable group: methacrylic group, acrylic equivalent: $1.2 \times 10^3$ g/eq, maximum absorption wavelength: 559 nm, produced by FUJIFILM Wako Pure Chemical Corporation), R60 (color: red, polymerizable group: methacrylic group, acrylic equivalent: $1.2 \times 10^3$ g/eq, maximum absorption wavelength: 499 nm, produced by FUJIFILM Wako Pure Chemical Corporation), K01 (color: black, polymerizable group: methacrylic group, acrylic equivalent: $1.3 \times 10^3$ g/eq, produced by FUJIFILM Wako Pure Chemical Corporation), or the like; a cyanine-based dye such as Y03 (color: yellow, polymerizable group: methacrylic group, acrylic equivalent: $1.1 \times 10^3$ g/eq, maximum absorption wavelength: 419 nm, produced by FUJIFILM Wako Pure Chemical Corporation), or the like; a triarylmethane-based dye such as G01 (color: green, polymerizable group: methacrylic group, acrylic equivalent: $1.2 \times 10^3$ g/eq, maximum absorption wavelength: 643 nm, produced by FUJIFILM Wako Pure Chemical Corporation), B01 (color: blue, polymerizable group: methacrylic group, acrylic equivalent: $1.2 \times 10^3$ g/eq, maximum absorption wavelength: 624 nm, produced by FUJIFILM Wako Pure Chemical Corporation), or the like; and the like.

A method of forming the coating layer 1 on the polymer substrate is not particularly limited, and a known method can be applied as it is or after appropriate modification. For example, it is possible to use a method of preparing a coating liquid (coating liquid (1)) containing a protein adsorbent and a fluorescent dye, and applying the coating liquid (1) to the polymer substrate. Alternatively, in a case where a layer containing a protein adsorbent (cell adhesion factor) has been formed on a polymer substrate in advance as in a bioreactor or the like, for example, the coating layer 1 can be formed by preparing a coating liquid (coating liquid (1')) containing a fluorescent dye and applying the coating liquid (1') to the coating layer containing the protein adsorbent (cell adhesion factor) formed on the polymer substrate. That is, in a case where a coating layer containing a protein adsorbent has been formed on a polymer substrate in advance, in the step (1), a coating layer containing a fluorescent dye is formed on a surface of the coating layer containing the protein adsorbent of the polymer substrate having the coating layer, or a fluorescent dye is added to the coating layer containing the protein adsorbent and formed on the polymer substrate having the coating layer, thereby preparing the substrate 1. The substrate 1 is irradiated with light to detect a color development state 1 of the substrate 1.

Here, a solvent used for preparing the coating liquids (1) and (1') is not particularly limited, and can be appropriately selected depending on types of protein adsorbent and fluorescent dye. Specifically, examples of the solvent can include water; ketone-based solvents such as acetone, methyl ethyl ketone, methyl isobutyl ketone, cyclohexanone, or the like; ester-based solvents such as butyl acetate, ethyl acetate, carbitol acetate, butyl carbitol acetate, or the like; ether-based solvents such as methyl cellosolve, ethyl cellosolve, butyl ether, tetrahydrofuran, or the like; alkane-based solvents such as butane, hexane, or the like; aromatic-based solvents such as benzene, toluene, xylene, or the like; halogen-based solvents such as dichloroethane, chloroform, methylene chloride, or the like; alcoholic solvent such as methanol, ethanol, n-propanol, isopropanol, ethylene glycol, or the like; and the like. The solvents may be used alone or in combination of two or more thereof. In addition, the coating liquid (1) may be obtained by dissolving the protein adsorbent and the fluorescent dye in the same solvent, or the coating liquid (1) may be obtained by separately dissolving the protein adsorbent and the fluorescent dye in solvents, and mixing the solutions with each other. A mixing ratio of the protein adsorbent and the fluorescent dye in the coating liquid (1) is not particularly limited. The mixing ratio of the protein adsorbent and the fluorescent dye (a weight ratio of protein adsorbent:fluorescent dye) is preferably 2 to 200:1, and more preferably 7.5 to 150:1, from the viewpoint of balance between adhesion of a desired protein and fluorescence intensity (easy observation) or the like. A concentration of the protein adsorbent in the coating liquid (1) is not particularly limited, but is preferably 0.05 to 2 wt %, and more preferably 0.05 to 1 wt %. In addition, a concentration of the fluorescent dye in each of the coating liquids (1) and (1') is not particularly limited, but is preferably in the range of 0.005 to 0.1 wt %, and more preferably in the range of 0.01 to 0.05 wt %. In such ranges, coatability of each of the coating liquids (1) and (1') is excellent. In addition, a uniform coating layer 1 having a desired thickness can be easily obtained with one coating.

A coating amount of the coating liquid (1) is not particularly limited, but is preferably an amount such that a thickness (dry film thickness) of the coating layer 1 is 1 to 5 μm. In addition, a coating amount of the coating liquid (1') is not particularly limited, but is preferably such an amount that the coating layer 1 can sufficiently fluoresce by being irradiated with light. Specifically, the coating amount of the coating liquid (1') is preferably such an amount as of 0.15 to 0.45 g/cm$^3$ coating layer 1.

Before applying the coating liquid (1), a surface of a polymer substrate may be subjected to a pre-treatment such as an ultraviolet irradiation treatment, a plasma treatment, a corona discharge treatment, a flame treatment, an oxidation treatment, a silane coupling treatment, a phosphoric acid coupling treatment, or the like. For example, the polymer substrate surface is hydrophilized by subjecting the surface of the polymer substrate to plasma treatment. By doing so, wettability of the coating liquid (1) to the polymer substrate surface can be improved and a uniform coating layer 1 can thus be formed.

A method of applying the coating liquid (1) or (1') to the polymer substrate is not particularly limited, and it is possible to apply a method known in the related art such as a coating-printing method, an immersion method (a dipping method or a dip coating method), a spray method, a spin coating method, a mixed solution impregnation sponge coating method, or the like. Among them, an immersion method (a dipping method or a dip coating method) is preferable. Alternatively, in a case of a bioreactor or the like, the coating liquid (1) or (1') may be introduced into or circulated in the polymer substrate in the bioreactor.

After applying the coating liquid (1) to the polymer substrate, a coated film is preferably dried. Here, dry conditions are not particularly limited as long as the solvent is removed from the coated film, and the coated film may be subjected to warm air treatment using a drier or the like, or may be naturally dried. Alternatively, in a case of a bioreactor or the like, dried air may be introduced into or circulated in the bioreactor. In addition, a pressure condition at the time of drying is not particularly limited, and the drying may be performed under normal pressure (atmospheric pressure) or under an elevated pressure or under a reduced pressure. As drying means (apparatus), for example, an oven, a vacuum dryer, or the like can be used, but in a case of natural drying, drying means (apparatus) is not particularly necessary.

By the above method, the coating layer 1 is formed on the polymer substrate to obtain the substrate 1. Next, the color development state 1 of the substrate 1 is detected by irradiating the substrate 1 thus obtained with light.

Here, light to be irradiated is appropriately selected depending on a type of fluorescent reagent. Specifically, ultraviolet (UV) rays, visible rays, infrared rays, electron beams, gamma rays, or the like can be used. UV rays or electron beams are preferable, and UV rays are more preferable, in consideration of an influence on a human body. When irradiating UV rays, as an irradiation wavelength, a wavelength that can excite a fluorescent dye can be appropriately selected. Specifically, a wavelength range of UV rays is preferably 200 to 400 nm, and more preferably 220 to 320 nm. In addition, the irradiation with UV rays is preferably performed at a temperature of 10 to 50° C. and more preferably 20 to 40° C. An irradiation intensity of UV rays is not particularly limited, but is preferably 1 to 5,000 mW/cm$^2$, more preferably 1 to 100 mW/cm$^2$, and still more preferably 1 to 10 mW/cm$^2$. In addition, an integrated light quantity of UV rays (integrated light quantity of UV rays to a substrate 1 before a surface lubricating layer is applied) is not particularly limited, but is preferably 1 to 5,000 mJ/cm$^2$, and more preferably 1 to 100 mJ/cm$^2$. Examples of an apparatus irradiating UV rays can include a high pressure mercury lamp, a low-pressure mercury lamp, a metal halide lamp, a xenon lamp, a halogen lamp, or the like.

By the irradiation, the fluorescent dye in the coating layer 1 is developed, and a color development state (color development state 1) is detected (FIG. 1).

[Step (2)]

In the present step, the substrate 2 in which the coating layer containing the protein adsorbent and the fluorescent dye and the coating layer containing the protein detection reagent are sequentially formed on at least one surface of the polymer substrate is prepared, and the color development state 2 of the substrate 2 is detected by irradiating the substrate 2 with light. It should be noted that, hereinafter, the "coating layer containing the protein adsorbent and the fluorescent dye" and the "coating layer containing the protein detection reagent" in the present step (2) are simply referred to as a "coating layer 1'" and a "coating layer 2'", respectively.

The polymer substrate is not particularly limited, and a substrate required for evaluation of a coating state of a protein adsorbent or an adsorption state of a protein can be used. Specifically, the same polymer substrate as that in the step (1) can be used. The polymer substrate used in the present step (2) is preferably the same as that used in the step (1).

The coating layer containing a protein adsorbent and a fluorescent dye (coating layer 1') and the coating layer containing a protein detection reagent (coating layer 2') are formed on at least one surface of the polymer substrate to prepare the substrate 2.

The coating layer 1' may be formed on at least one surface required for evaluation of a coating state of a protein adsorbent or an adsorption state of a protein, but is preferably formed on only one surface. In addition, it is not necessary to form the coating layer on the entire surface of the polymer substrate, and the coating layer 1' is formed in at least a portion required for evaluation of a coating state of a protein adsorbent or an adsorption state of a protein. Preferably, the coating layer 1' is formed on the entire surface of the polymer substrate. The coating layer 1' is preferably formed in the same manner as that of the coating layer 1 from the viewpoint of easier and more accurate comparison between the color development states or the like.

The protein adsorbent used in the coating layer 1' is not particularly limited as long as it has protein adsorbability. Specifically, since the same protein adsorbent as that in the step (1) can be used, the description thereof is omitted here. The protein adsorbent used in the coating layer 1' is particularly preferably the same as that used in the coating layer 1, from the viewpoint of easier and more accurate comparison between the color development states or the like.

The fluorescent dye used in the coating layer 1' is not particularly limited as long as it is excited when being irradiated with light such as ultraviolet rays or the like and emits inherent fluorescence. Specifically, since the same fluorescent dye as that in the step (1) can be used, the description thereof is omitted here. The fluorescent dye used in the coating layer 1' is preferably the same as that used in the coating layer 1, from the viewpoint of easier and more accurate comparison between the color development states or the like.

A method of forming the coating layer 1' on the polymer substrate is not particularly limited, and a known method can be applied as it is or after appropriate modification. Specifically, since the same method as that in the step (1) can be used, the description thereof is omitted here. The coating layer 1' is preferably formed on the polymer substrate in the same manner as that of the coating layer 1 from the viewpoint of easier and more accurate comparison between the color development states or the like.

A method of forming the coating layer 1' on the polymer substrate is not particularly limited, and a known method can be applied as it is or after appropriate modification. Specifically, since the same method as that in the step (1) can be used, the description thereof is omitted here. In a case where a layer containing a protein adsorbent (cell adhesion factor) has been formed on a polymer substrate in advance as in a bioreactor or the like, for example, the coating layer 1' can be formed by preparing a coating liquid (coating liquid (1')) containing a fluorescent dye and applying the coating liquid (1') to the coating layer containing the protein adsorbent (cell adhesion factor) formed on the polymer substrate. That is, in a case where a substrate has a coating layer containing a protein adsorbent, in the step (2), a substrate 2 in which a coating layer containing a fluorescent dye and a coating layer containing a protein detection reagent are sequentially formed on a surface of the coating layer containing the protein adsorbent of the polymer substrate having the coating layer is prepared. The substrate 2 is irradiated with light to detect a color development state 2 of the substrate 2. The coating layer 1' is preferably formed on the polymer substrate in the same manner as that of the coating layer 1 from the viewpoint of easier and more accurate comparison between the color development states or the like.

That is, the coating layer 1' is preferably the same as the coating layer 1.

Next, a coating layer containing a protein detection reagent (coating layer 2') is disposed on the coating layer 1'. Here, the coating layer 2' may be formed on at least a surface required for evaluation of a coating state of a protein adsorbent or an adsorption state of a protein, but is preferably formed in at least a portion of the coating layer 1', and is more preferably formed on the entire surface of the coating layer 1'.

The protein detection reagent used in the coating layer 2' is not particularly limited as long as it has protein detection ability, and can be appropriately selected depending on a type of protein to be detected. Specifically, bicinchoninic acid, Coomassie blue, ninhydrin, or the like can be used. Among them, the protein detection reagent preferably has a quinoline structure, and is more preferably bicinchoninic acid (BCA). In a preferred embodiment, the protein is detected by a bicinchoninic acid method (BCA method). In the BCA method, a peptide bond of a protein reduces cupric ions ($Cu^{2+}$) to generate a tetradentate cuprous ion ($Cu^{1+}$) complex under an alkaline condition, and the cuprous ion complex reacts with BCA (two BCA molecules per $Cu^{1+}$) to exhibit a strong purple color. Therefore, in the BCA method, a protein can be measured in 562 nm. The BCA method is preferably used in terms of high protein detection ability, high compatibility against an interfering compound, easiness, a wide linear action range (excellent in quantification), or the like. In addition, it is also preferable in terms of a wide overlapping region between an absorption spectrum of bicinchoninic acid (BCA) and an excitation spectrum of a xanthene-based fluorescent dye.

A method of forming the coating layer 2' on the coating layer 1' is not particularly limited, and a known method can be applied as it is or after appropriate modification. For example, it is possible to use a method of preparing a coating liquid (coating liquid (2)) containing a protein detection reagent, and applying the coating liquid (2) to the coating layer 1'. Here, a solvent used for preparing the coating liquid (2) is not particularly limited as long as it can dissolve the protein detection reagent. Specifically, it is possible to use the same solvent as used in the preparation of the coating liquid (1) in the step (1). A concentration of the protein detection reagent in the coating liquid (2) is not particularly limited, but is preferably in the range of 2.0 to 20.0 wt %, and more preferably in the range of 5.0 to 15.0 wt %. In such ranges, coatability of the coating liquid (2) is excellent. In addition, a uniform coating layer 2' having a desired thickness can be easily obtained with one coating.

A coating amount of the coating liquid (2) is not particularly limited, but is preferably an amount such that a thickness (dry film thickness) of the coating layer 2' is 0.1 to 2 µm. Alternatively, the coating amount of the coating liquid (2) is preferably such an amount as of 0.1 to 0.3 g/cm$^3$ coating layer 2'.

A method of applying the coating liquid (2) to the coating layer 1' is not particularly limited, and a method that is the same as the coating method of the coating liquid (1) in the step (1) can be applied. Among them, an immersion method (a dipping method or a dip coating method) is preferable. Alternatively, in a case of a bioreactor or the like, the coating liquid (2) may be introduced into or circulated in the polymer substrate in the bioreactor.

After applying the coating liquid (2) to the coating layer 1', the coated film is preferably dried. Here, dry conditions are not particularly limited as long as the solvent is removed from the coated film, and the coated film may be subjected to warm air treatment using a drier or the like, or may be naturally dried. Alternatively, in a case of a bioreactor or the like, dried air may be introduced into or circulated in the bioreactor. In addition, a pressure condition at the time of drying is not particularly limited, and the drying may be performed under normal pressure (atmospheric pressure) or under an elevated pressure or a reduced pressure. As drying means (apparatus), for example, an oven, a vacuum dryer, or the like can be used, but in a case of natural drying, drying means (apparatus) is not particularly necessary.

By the above method, the coating layers 1' and 2' are sequentially formed on the polymer substrate to obtain the substrate 2. Next, the color development state 2 of the substrate 2 is detected by irradiating the substrate 2 thus obtained with light. Here, light to be irradiated is appropriately selected depending on a type of fluorescent reagent. Specifically, since the same light, irradiation conditions, and method as those in the step (1) can be used, the descriptions thereof are omitted here. The color development state 2 is particularly preferably detected in the same method and conditions as those in the step (1), from the viewpoint of easier and more accurate comparison between the color development states or the like.

Figure 2:
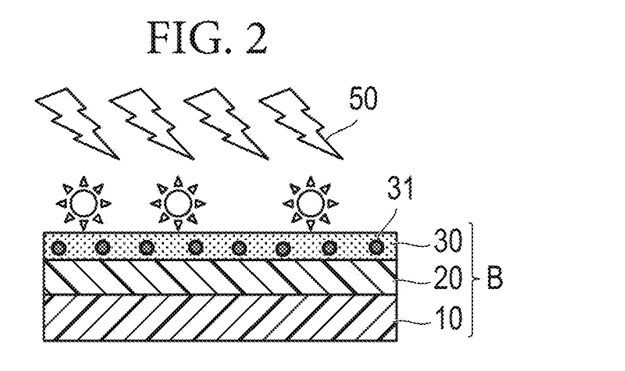
FIG. 2 is a view of a substrate B in which a coating layer containing a protein adsorbent and a fluorescent dye and a coating layer containing a protein detection reagent are sequentially formed on a polymer substrate.

By the irradiation, the fluorescent dye in the coating layer 1' is developed, and a color development state (color development state 2) is detected (FIG. 2).

[Step (3)]

In the present step, the substrate 3 in which the coating layer containing the protein adsorbent and the fluorescent dye is formed on at least one surface of the polymer substrate is prepared, the sample containing the protein is introduced into the substrate 3 to obtain the substrate 4, and the color development state 3 of the substrate 4 is detected by irradiating the substrate 4 with light. It should be noted that, hereinafter, the "coating layer containing the protein adsorbent and the fluorescent dye" in the present step (3) is simply referred to as a "coating layer 1'''".

The polymer substrate is not particularly limited, and a substrate required for evaluation of a coating state of a protein adsorbent or an adsorption state of a protein can be used. Specifically, the same polymer substrate as that in the step (1) can be used. The polymer substrate used in the present step (3) is preferably the same as that used in the step (1) or (2), and is more preferably the same as those used in the steps (1) and (2).

The coating layer containing a protein adsorbent and a fluorescent dye (coating layer 1'') is formed on at least one surface of the polymer substrate to prepare the substrate 3.

The coating layer 1'' may be formed on at least one surface required for evaluation of a coating state of a protein adsorbent or an adsorption state of a protein, but is preferably formed on only one surface. In addition, it is not necessary to form the coating layer on the entire surface of the polymer substrate, and the coating layer 1'' is formed in at least a portion required for evaluation of a coating state of a protein adsorbent or an adsorption state of a protein. Preferably, the coating layer 1'' is formed on the entire surface of the polymer substrate. The coating layer 1'' is preferably formed in the same manner as that of the coating layer 1 or 1', and is more preferably formed in the same manner as those of the coating layers 1 and 1', from the viewpoint of easier and more accurate comparison between the color development states or the like.

The protein adsorbent used in the coating layer 1'' is not particularly limited as long as it has protein adsorbability. Specifically, since the same protein adsorbent as that in the step (1) can be used, the description thereof is omitted here. The protein adsorbent used in the coating layer 1'' is preferably the same as that used in the coating layer 1 or 1', and is more preferably the same as those used in the coating layers 1 and 1', from the viewpoint of easier and more accurate comparison between the color development states or the like.

The fluorescent dye used in the coating layer 1'' is not particularly limited as long as it is excited when being irradiated with light such as ultraviolet rays or the like and emits inherent fluorescence. Specifically, since the same fluorescent dye as that in the step (1) can be used, the description thereof is omitted here. The fluorescent dye used in the coating layer 1'' is preferably the same as that used in the coating layer 1 or 1', and is more preferably the same as those used in the coating layers 1 and 1', from the viewpoint of easier and more accurate comparison between the color development states or the like.

A method of forming the coating layer 1'' on the polymer substrate is not particularly limited, and a known method can be applied as it is or after appropriate modification. Specifically, since the same method as that in the step (1) can be used, the description thereof is omitted here. The coating layer 1'' is preferably formed on the polymer substrate in the same manner as that of the coating layer 1 or 1', and is more preferably formed on the polymer substrate in the same manner as those of the coating layers 1 and 1', from the viewpoint of easier and more accurate comparison between the color development states or the like.

That is, the coating layer 1" is preferably the same as the coating layer 1 or the coating layer 1', and more preferably the same as the coating layer 1 and the coating layer 1'.

Next, the sample containing a protein is introduced into the substrate 3 in which the coating layer 1" has been formed on the polymer substrate (substrate 4). By doing so, the protein is adsorbed to the protein adsorbent in the coating layer 1".

Here, the protein is not particularly limited, and examples thereof can include a protein itself, a mixture of proteins such as serum and the like, a cell(s), and the like. In addition, a method of introducing the sample is not particularly limited as long as the protein in the sample can be in contact with the coating layer 1" (protein adsorbent). Specifically, an example thereof can include impregnation of the substrate 3 with the sample and coating of the sample on the substrate 3, and the like. Alternatively, in a case of a bioreactor or the like, the sample may be introduced into or circulated in the substrate 3 (the polymer substrate having the coating layer 1" formed thereon) in the bioreactor.

Next, the color development state 3 of the substrate 4 is detected by irradiating the substrate 4 into which the sample containing the protein has been introduced with light. Here, light to be irradiated is appropriately selected depending on a type of fluorescent reagent. Specifically, since the same light, irradiation conditions, and method as those in the step (1) can be used, the descriptions thereof are omitted here. The color development state 3 is preferably detected in the same method and conditions as those in the step (1) or (2), and the color development state 3 is more preferably detected in the same method and conditions as those in the steps (1) and (2), from the viewpoint of easier and more accurate comparison between the color development states or the like.

By the irradiation, the fluorescent dye in the coating layer 1" is developed, and a color development state (color development state 3) is detected (FIG. 3).

[Step (4)]

In the present step, the substrate 5 in which the coating layer containing the protein adsorbent and the fluorescent dye is formed on at least one surface of the polymer substrate is prepared, the sample containing the protein is introduced into the substrate 5 to obtain the substrate 6, the protein detection reagent is introduced into the substrate 6 to obtain the substrate 7, and the color development state 4 of the substrate 7 is detected by irradiating the substrate 7 with light. It should be noted that, hereinafter, the "coating layer containing the protein adsorbent and the fluorescent dye" in the present step (4) is simply referred to as a "coating layer 1'''".

The polymer substrate is not particularly limited, and a substrate required for evaluation of a coating state of a protein adsorbent or an adsorption state of a protein can be used. Specifically, the same polymer substrate as that in the step (1) can be used. The polymer substrate used in the present step (4) is preferably the same as that used in the step (1), (2), or (3), and is more preferably the same as those used in the steps (1), (2), and (3).

The coating layer containing a protein adsorbent and the fluorescent dye (coating layer 1''') is formed on at least one surface of the polymer substrate to prepare the substrate 5.

The coating layer 1''' may be formed on at least one surface required for evaluation of a coating state of a protein adsorbent or an adsorption state of a protein, but is preferably formed on only one surface. In addition, it is not necessary to form the coating layer on the entire surface of the polymer substrate, and the coating layer 1''' is formed in at least a portion required for evaluation of a coating state of a protein adsorbent or an adsorption state of a protein.

Preferably, the coating layer 1''' is formed on the entire surface of the polymer substrate. The coating layer 1''' is preferably formed in the same manner as that of the coating layer 1, the coating layer 1', or the coating layer 1", and is more preferably formed in the same manner as those of the coating layer 1, the coating layer 1', and the coating layer 1", from the viewpoint of easier and more accurate comparison between the color development states or the like.

The protein adsorbent used in the coating layer 1''' is not particularly limited as long as it has protein adsorbability. Specifically, since the same protein adsorbent as that in the step (1) can be used, the description thereof is omitted here. The protein adsorbent used in the coating layer 1''' is preferably the same as that used in the coating layer 1, the coating layer 1', or the coating layer 1", and is more preferably the same as those used in the coating layer 1, the coating layer 1', and the coating layer 1", from the viewpoint of easier and more accurate comparison between the color development states or the like.

The fluorescent dye used in the coating layer 1''' is not particularly limited as long as it is excited when being irradiated with light such as ultraviolet rays or the like and emits inherent fluorescence. Specifically, since the same fluorescent dye as that in the step (1) can be used, the description thereof is omitted here. The fluorescent dye used in the coating layer 1''' is preferably the same as that used in the coating layer 1, the coating layer 1', or the coating layer 1", and is more preferably the same as those used in the coating layer 1, the coating layer 1', and the coating layer 1", from the viewpoint of easier and more accurate comparison between the color development states or the like.

A method of forming the coating layer 1''' on the polymer substrate is not particularly limited, and a known method can be applied as it is or after appropriate modification. Specifically, since the same method as that in the step (1) can be used, the description thereof is omitted here. The coating layer 1''' is preferably formed on the polymer substrate in the same manner as that of the coating layer 1, the coating layer 1', or the coating layer 1", and is more preferably formed on the polymer substrate in the same manner as those of the coating layer 1, the coating layer 1', and the coating layer 1", from the viewpoint of easier and more accurate comparison between the color development states or the like.

That is, the coating layer 1''' is preferably the same as the coating layer 1, the coating layer 1', or the coating layer 1", and more preferably the same as the coating layer 1, the coating layer 1', and the coating layer 1".

Next, the sample containing the protein is introduced into the substrate 5 in which the coating layer 1''' has been formed on the polymer substrate (substrate 6). By doing so, the protein is adsorbed to the protein adsorbent in the coating layer 1'''.

Here, a method of introducing the sample is not particularly limited as long as the protein in the sample can be in contact with the coating layer 1''' (protein adsorbent). Specifically, since the same method as in the step (3) can be used, the description thereof is omitted here. The sample is preferably introduced by the same method as that in the step (3) from the viewpoint of easier and more accurate comparison between the color development states or the like.

Next, the protein detection reagent is introduced into the substrate 6 into which the sample containing the protein has been introduced (substrate 7). The protein detection reagent used here is not particularly limited as long as it can detect a protein present in the substrate 6, is appropriately selected depending on a type of protein to be detected. Specifically, since the same protein detection reagent as in the step (2) can be used, the description thereof is omitted here. The protein detection reagent is particularly preferably the same as that used in the coating layer 2', from the viewpoint of easier and more accurate comparison between the color development states or the like. That is, the protein detection reagent preferably has a quinoline structure, and is more preferably bicinchoninic acid (BCA).

Next, the color development state 4 of the substrate 7 is detected by irradiating the substrate 7 into which the protein detection reagent has been introduced with light. Here, light to be irradiated is appropriately selected depending on a type of fluorescent reagent. Specifically, since the same light, irradiation conditions, and method as those in the step (1) can be used, the descriptions thereof are omitted here. The type of light, the irradiation conditions, and the method are preferably the same as those in the step (1), (2), or (3), and more preferably the same as those in the steps (1), (2), and (3), from the viewpoint of easier and more accurate comparison between the color development states or the like.

By the irradiation, the fluorescent dye in the coating layer 1''' is developed, and a color development state (color development state 4) is detected (FIG. 4).

[Step (5)]

In the present step, the coating state of the protein adsorbent or the adsorption state of the protein is evaluated by comparing the color development state 4 detected in the step (4) with the color development state 1 detected in the step (1), the color development state 2 detected in the step (2), or the color development state 3 detected in the step (3).

As mentioned above, in a case where the proteins are adsorbed in the same amount, a degree of emission (fluorescence intensity) in each of the color development states 1 to 4 is high in the order of the color development state 1, the color development state 3, the color development state 2, and the color development state 4 (color development state 4<color development state 2<color development state 3<color development state 1). Therefore, in a case where the fluorescence intensity in the color development state 4 is low as compared with the color development state 1, 2, or 3, it can be evaluated that the protein is adsorbed on the substrate or the protein adsorbent is effectively present on the polymer substrate. That is, in the case where the fluorescence intensity in the color development state 4 is low as compared with the color development state 1, 2, or 3, the coating state of the protein adsorbent and the adsorption state of the protein can be evaluated. In one embodiment of the present invention, in a case where light absorption of the fluorescent dye is suppressed in the color development state 4 as compared with the color development state 1, 2, or 3, it is evaluated that the protein is adsorbed on the substrate or the protein adsorbent is coated on the polymer substrate.

In the present step, as mentioned above, a difference between the color development state 4 and the color development state 1 or 3 is relatively large. Therefore, the color development state 4 is preferably compared with the color development state 1 or 3, and more preferably compared with the color development state 1, from the viewpoint of easier comparison or the like. Here, in a case of a bioreactor in which the layer containing the protein adsorbent (cell adhesion factor) has been formed on the polymer substrate in advance or the like, the coating state of the protein adsorbent (cell adhesion factor) can be easily evaluated by a simple operation of circulating the coating liquid containing the fluorescent dye (color development state 1), sequentially circulating the coating liquid containing the fluorescent dye and the sample containing the protein (color development state 3), or sequentially circulating the coating liquid containing the fluorescent dye, the sample containing the protein, and the coating liquid containing the protein detection reagent (color development state 4), in the coating layer containing the protein adsorbent (cell adhesion factor) formed on the polymer substrate.

After evaluating the coating state of the protein adsorbent or the adsorption state of the protein in the step (4), each of the substrates (substrates 1, 2, 4, and 7) may be washed with a buffer solution such as physiological saline, a phosphate buffer solution or the like, water such as ion-exchange water, pure water, RO water, or the like.

According to the method of the present invention, it is possible to simply and quickly visualize the coating state of the protein adsorbent or the adsorption state of the protein by comparing the color development state after introducing the protein. For example, regarding the color development state 4, in a case where the fluorescence intensity on the entire surface of the polymer substrate is uniform, it can be evaluated that the protein adsorbent is uniformly present on the polymer substrate. In addition, the method is not limited by a structure of the substrate. Therefore, according to the method of the present invention, whether or not the cell adhesion factor (protein adsorbent) can be uniformly disposed on the hollow fiber membrane can be evaluated by a nondestructive test even for a cell container having a diversified and complicated structure (shape) such as the above hollow fiber type bioreactor or the like.

In addition, the fluorescence intensity in each of the color development states 3 to 4 is proportional to an amount of protein. That is, for a desired protein whose presence/absence is to be confirmed, a calibration curve of fluorescence intensity with respect to an amount of the protein is created by using proteins whose amounts are known, and an amount of the protein in the sample can be measured based on the calibration curve and the fluorescence intensity in the color development state 4. Specifically, samples having a known amount of protein are each subjected to the same operation as that of the above (step (4)), and fluorescence intensities of the protein are measured, thereby creating a calibration curve of protein amount and fluorescence intensity. Here, the measurement method of the fluorescence intensity is not particularly limited, and a known method can be used. For example, a fluorescence measuring device (fluorescence scanner) or an image processing system can be used. The calibration curve to be obtained is effective as a calibration curve because it is constant regardless of external factors. Therefore, the protein amount in the sample can be accurately measured by using the calibration curve.

EXAMPLES

The effects of the present invention will be described by using the following examples and comparative examples. However, the technical scope of the present invention is not limited to only the following examples. Incidentally, in the following examples, the operation was performed at room temperature (25° C.), unless otherwise specified. In addition, unless otherwise specified, "%" and "part(s)" refer to "wt %" and "part(s) by weight", respectively.

Production Example 1: Synthesis of Protein Adsorbent (pTHFA) 1

Polytetrahydrofurfuryl acrylate (pTHFA) 1 (weight average molecular weight: 600,000) was synthesized by the following method.

A 300 mL four-necked flask was charged with 90 g of methanol (produced by FUJIFILM Wako Pure Chemical Corporation). Next, 60 g of tetrahydrofurfuryl acrylate (THFA) was added to the four-necked flask, and the mixture was stirred and bubbled with nitrogen gas for about 1 hour, thereby preparing a 40 wt % THFA solution. Further, 0.06 g of 2,2'-azobis(4-methoxy-2,4-dimethylvaleronitrile (produced by FUJIFILM Wako Pure Chemical Corporation, V-70) was added to the THFA solution as a polymerization initiator, to carry out radical polymerization reaction in an oil bath at 45° C. for 6 hours. After the reaction for a predetermined time, the reaction product was transferred to a beaker and allowed to stand for 3 to 4 hours to precipitate a polymer (polytetrahydrofurfuryl acrylate), and a supernatant was discarded. Next, acetone was added to the beaker and the mixture was stirred to dissolve the polymer, and the solution was added dropwise into cyclohexane to reprecipitate the polymer. The precipitate was collected and dried under vacuum at 60° C. overnight, to obtain polytetrahydrofurfuryl acrylate (pTHFA) 1. A weight average molecular weight (Mw) of the resulting polytetrahydrofurfuryl acrylate (pTHFA) 1 was measured, to be about 600,000.

Production Example 2: Synthesis of Protein Adsorbent (pTHFA) 2

Polytetrahydrofurfuryl acrylate (pTHFA) 2 (weight average molecular weight: 200,000) was synthesized by the following method.

A 300 mL four-necked flask was charged with 190 g of methanol (produced by FUJIFILM Wako Pure Chemical Corporation). Next, 60 g of tetrahydrofurfuryl acrylate (THFA) was added to the four-necked flask, and the mixture was stirred and bubbled with nitrogen gas for about 1 hour, thereby preparing a 24 wt % THFA solution. Further, 0.06 g of 2,2'-azobis(4-methoxy-2,4-dimethylvaleronitrile (produced by FUJIFILM Wako Pure Chemical Corporation, V-70) was added to the THFA solution as a polymerization initiator, to carry out radical polymerization reaction in an oil bath at 45° C. for 6 hours. After the reaction for a predetermined time, the reaction product was transferred to a beaker and allowed to stand for 3 to 4 hours to precipitate a polymer (polytetrahydrofurfuryl acrylate), and a supernatant was discarded. Next, acetone was added to the beaker and the mixture was stirred to dissolve the polymer, and the solution was added dropwise into cyclohexane to reprecipitate the polymer. The precipitate was collected and dried under vacuum at 60° C. overnight, to obtain polytetrahydrofurfuryl acrylate (pTHFA) 2. A weight average molecular weight (Mw) of the resulting polytetrahydrofurfuryl acrylate (pTHFA) 2 was measured, to be about 200,000.

Production Example 3: Synthesis of Protein Adsorbent (pTHFA) 3

Polytetrahydrofurfuryl acrylate (pTHFA) 3 (weight average molecular weight: 100,000) was synthesized by the following method.

A 300 mL four-necked flask was charged with 220 g of methanol (produced by FUJIFILM Wako Pure Chemical Corporation). Next, 30 g of tetrahydrofurfuryl acrylate (THFA) was added to the four-necked flask, and the mixture was stirred and bubbled with nitrogen gas for about 1 hour, thereby preparing a 12 wt % THFA solution. Further, 0.06 g of 2,2'-azobis(4-methoxy-2,4-dimethylvaleronitrile (produced by FUJIFILM Wako Pure Chemical Corporation, V-70) was added to the THFA solution as a polymerization initiator, to carry out radical polymerization reaction in an oil bath at 45° C. for 6 hours. After the reaction for a predetermined time, the reaction product was transferred to a beaker and allowed to stand for 3 to 4 hours to precipitate a polymer (polytetrahydrofurfuryl acrylate), and a supernatant was discarded. Next, acetone was added to the beaker and the mixture was stirred to dissolve the polymer, and the solution was added dropwise into cyclohexane to reprecipitate the polymer. The precipitate was collected and dried under vacuum at 60° C. overnight, to obtain polytetrahydrofurfuryl acrylate (pTHFA) 3. A weight average molecular weight (Mw) of the resulting polytetrahydrofurfuryl acrylate (pTHFA) 3 was measured, to be about 100,000.

Example 1

Detection of Color Development State 1

3 g of pTHFA 3 (Mw=100,000) (protein adsorbent) obtained in Production Example 3 was mixed with 300 g of methanol to obtain a pTHFA solution. To the pTHFA solution, 20 mg of a polymerizable dye fluorescent purple R13 (color: fluorescent purple, polymerizable group: methacrylic group, acrylic equivalent: $1.2 \times 10^3$ g/eq, maximum absorption wavelength: 559 nm, produced by FUJIFILM Wako Pure Chemical Corporation) (fluorescent dye) was added, thereby obtaining a dispersion.

10 mL of the dispersion was cast in a Petri dish and naturally dried in a draft for 4 hours to form a film (dry film thickness: 2 μm) (substrate A-1) containing pTHFA and R13 in the Petri dish (Petri dish A). The substrate A-1 was taken out from the Petri dish A to prepare a substrate A.

The substrate A was irradiated with ultraviolet (UV) rays with a low-pressure mercury lamp under irradiation conditions of a wavelength of 254 nm, irradiation intensity of 2.02 mW/cm², an irradiation distance of 50 mm, and an integrated light quantity of 2.02 mJ/cm².

Detection of Color Development State 2

Bicinchoninic acid (BCA) which is a protein detection reagent was added to a copper ion chelating agent (composition: bicinchoninic acid Cu⁺ complex, produced by Thermo Fisher Scientific Inc., trade name: BCA Protein Assay) so that a concentration thereof was 1 wt %, thereby preparing a BCA solution.

A substrate A-1 was prepared in a Petri dish (Petri dish A) in the same manner as that of the above (Detection of Color Development State 1). 10 mL of the BCA solution was cast and naturally dried in a draft for a day in the Petri dish A to form a BCA film (dry film thickness: 1 μm) (substrate B-1) on the substrate A-1. The substrate B-1 was taken out from the Petri dish to prepare a substrate B.

The substrate B was irradiated with ultraviolet (UV) rays with a low-pressure mercury lamp under irradiation conditions of a wavelength of 254 nm, irradiation intensity of 2.02 mW/cm², an irradiation distance of 50 mm, and an integrated light quantity of 2.02 mJ/cm².

Detection of Color Development State 3

Fetal bovine serum (FBS) was added to a phosphate buffer solution (PBS, pH=7.4) so that a concentration thereof was 10 vol % to prepare a protein solution.

A substrate A-1 was prepared in a Petri dish (Petri dish A) in the same manner as that of the above (Detection of Color Development State 1). 50 mL of the protein solution was poured to the Petri dish A and left for 30 minutes. After a predetermined time was elapsed, the protein solution was discarded from the Petri dish A (Petri dish C-1). The Petri dish C-1 was washed with 50 mL of phosphate-buffered physiological saline (PBS, pH 7.4) three times (Petri dish C-2). After the washing, the Petri dish C-2 was naturally dried in a draft for 4 hours to obtain a substrate C-1 in the Petri dish (Petri dish C-3). The substrate C-1 was taken out from the Petri dish C-3 to prepare a substrate C.

The substrate C was irradiated with ultraviolet (UV) rays with a low-pressure mercury lamp under irradiation conditions of a wavelength of 254 nm, irradiation intensity of 2.02 mW/cm$^2$, an irradiation distance of 50 mm, and an integrated light quantity of 2.02 mJ/cm$^2$.

Detection of Color Development State 4

A BCA solution was prepared in the same manner as that of the above (Detection of Color Development State 2).

A substrate C-1 was prepared in a Petri dish (Petri dish C-3) in the same manner as that of the above (Detection of Color Development State 3). 10 mL of the BCA solution was added to the Petri dish C-3 and incubated at 37° C. for 1 hour to react FBS and BCA with each other (substrate D-1). The substrate D-1 was taken out from the Petri dish to prepare a substrate D.

The substrate D was irradiated with ultraviolet (UV) rays with a low-pressure mercury lamp under irradiation conditions of a wavelength of 254 nm, irradiation intensity of 2.02 mW/cm$^2$, an irradiation distance of 50 mm, and an integrated light quantity of 2.02 mJ/cm$^2$.

The fluorescence in the color development state 4 of the substrate D is significantly quenched as compared with the color development state 1 of the substrate A, the color development state 2 of the substrate B, and the color development state 3 of the substrate C. Also, the fluorescence in the substrate D is entirely quenched. Therefore, it is considered that pTHFA which is a protein adsorbent is uniformly disposed on the entire surface of the substrate D. In addition, it is expected that an amount of protein in the coating layer can be measured by measuring an absorption spectrum (fluorescence intensity).

It is considered from the above results that, according to the method of the present invention, the coating state of the protein adsorbent or the adsorption state of the protein can be easily and quickly visualized. Further, it is considered that, according to the method of the present invention, the coating state of the protein adsorbent or the adsorption state of the protein can be visualized by a nondestructive test even on a substrate having a complicated structure.

Example 2

Detection of Color Development State 1

A PAES/PVP/PA porous hollow fiber membrane with an inner diameter of 215±10 μm and an inner thickness of 50±5 μm was placed in a housing to prepare a bioreactor 1 having a membrane area of 2.1 m$^2$.

3 g of pTHFA 3 (Mw=100,000) (protein adsorbent) obtained in Production Example 3 was mixed with 300 g of methanol to obtain a pTHFA solution. To the pTHFA solution, 20 mg of a polymerizable dye fluorescent purple R13 (color: fluorescent purple, polymerizable group: methacrylic group, acrylic equivalent: 1.2×10$^3$ g/eq, maximum absorption wavelength: 559 nm, produced by FUJIFILM Wako Pure Chemical Corporation) (fluorescent dye) was added, thereby obtaining a dispersion.

The dispersion was circulated in a cavity of the hollow fiber membrane of the bioreactor 1 at a rate of 20 ml/min with a rotary pump for 30 minutes and was incubated at 37° C. for 1 hour, thereby forming a coating layer X containing pTHFA and R13 on an inner surface of the hollow fiber membrane (bioreactor 1').

The bioreactor 1' was irradiated with ultraviolet (UV) rays with a low-pressure mercury lamp under irradiation conditions of a wavelength of 254 nm, irradiation intensity of 2.02 mW/cm$^2$, an irradiation distance of 50 mm, and an integrated light quantity of 2.02 mJ/cm$^2$.

Detection of Color Development State 3

Fetal bovine serum (FBS) was added to a phosphate buffer solution (PBS, pH=7.4) so that a concentration thereof was 10% to prepare a protein solution.

The protein solution was circulated in a cavity of the hollow fiber membrane of the bioreactor 1' prepared as described above at a rate of 20 ml/min with a rotary pump for 30 minutes and was incubated at 37° C. for 1 hour (bioreactor 2). The bioreactor 2 was irradiated with ultraviolet (UV) rays with a low-pressure mercury lamp under irradiation conditions of a wavelength of 254 nm, irradiation intensity of 2.02 mW/cm$^2$, an irradiation distance of 50 mm, and an integrated light quantity of 2.02 mJ/cm$^2$.

Detection of Color Development State 4

Bicinchoninic acid (BCA) which is a protein detection reagent was added to a copper ion chelating agent (composition: bicinchoninic acid Cu$^+$ complex, produced by Thermo Fisher Scientific Inc., trade name: BCA Protein Assay) so that a concentration thereof was 10 wt %, thereby preparing a BCA solution.

A bioreactor 2 was prepared in the same manner as that of the above (Detection of Color Development State 3). The BCA solution prepared as described above was circulated in a cavity of the hollow fiber membrane of the bioreactor 2 at a rate of 20 ml/min with a rotary pump for 30 minutes and was held in an incubator of 37° C. for 1 hour (bioreactor 3). The bioreactor 3 was irradiated with ultraviolet (UV) rays with a low-pressure mercury lamp under irradiation conditions of a wavelength of 254 nm, irradiation intensity of 2.02 mW/cm$^2$, an irradiation distance of 50 mm, and an integrated light quantity of 2.02 mJ/cm$^2$.

The fluorescence in the color development state 4 of the bioreactor 3 is significantly quenched as compared with the color development state 1 of the bioreactor 1' or the color development state 3 of the bioreactor 2. Also, a pink-colored portion was observed in the color development state 4 of the bioreactor 3. It is presumed that the protein was not adsorbed in a particular portion (that is, the protein adsorbent is not sufficiently disposed). Therefore, it is expected that according to the method of the present invention, the coating state of the protein adsorbent can be easily confirmed. Furthermore, it is expected that an amount of protein in the coating layer can be measured by measuring an absorption spectrum (fluorescence intensity).

In addition, it is considered from the above results that, according to the method of the present invention, the coating state of the protein adsorbent or the adsorption state of the protein can be easily and quickly visualized. Further, it is considered that, according to the method of the present invention, the coating state of the protein adsorbent or the adsorption state of the protein can be visualized by a nondestructive test even on a substrate having a complicated structure.

Although embodiments of the present invention have been described and illustrated in detail, the disclosed embodiments are made for the purpose of illustration and example only and not limitation. The scope of the present invention should be interpreted by terms of the appended claims.

The entire disclosure of Japanese Patent Application No. 2019-172049, filed on Sep. 20, 2019, is incorporated herein by reference in its entirety.

The invention claimed is:

1. A method for evaluating a coating state of a protein adsorbent or an adsorption state of a protein, the method comprising:

providing a first substrate comprising a first coating layer and a polymer substrate, wherein the first coating layer of the first substrate comprises a protein adsorbent and a fluorescent dye and is formed on at least one surface of the polymer substrate;

irradiating the first substrate with light to detect a first color development state of the first substrate;

providing a second substrate comprising the first coating layer, the polymer substrate, and a second coating layer, wherein the first coating layer of the second substrate comprises the protein adsorbent and the fluorescent dye, wherein the second coating layer comprises a protein detection reagent, and wherein the first coating layer and the second coating layer are sequentially formed on at least one surface of the polymer substrate of the second substrate;

irradiating the second substrate with light to detect a second color development state of the second substrate;

providing a third substrate comprising the first coating layer and the polymer substrate, wherein the first coating layer of the third substrate comprises the protein adsorbent and the fluorescent dye, and wherein the first coating layer is formed on at least one surface of the polymer substrate of the third substrate;

introducing a sample comprising a protein onto the third substrate to obtain a fourth substrate;

irradiating the fourth substrate with light to detect a third color development state of the fourth substrate;

providing a fifth substrate comprising the first coating layer and the polymer substrate, wherein the first coating layer of the fifth substrate comprises the protein adsorbent and the fluorescent dye, and wherein the first coating layer is formed on at least one surface of the polymer substrate;

introducing the sample comprising the protein onto the fifth substrate to obtain a sixth substrate;

introducing the protein detection reagent onto the sixth substrate to obtain a seventh substrate;

irradiating the seventh substrate with light to detect a fourth color development state of the seventh substrate; and comparing the fourth color development state with the first color development state, the second color development state, and the third color development state to evaluate the coating state of the protein adsorbent or the adsorption state of the protein.

2. The method according to claim 1, wherein light absorption of the fluorescent dye is suppressed in the fourth color development state as compared with the first, second, or third color development states, and it is evaluated that the protein is adsorbed on the polymer substrate or the protein adsorbent is coated on the polymer substrate.

3. The method according to claim 2, wherein the protein detection reagent has a quinoline structure.

4. The method according to claim 3, wherein the protein detection reagent is bicinchoninic acid.

5. The method according to claim 3, wherein the protein adsorbent has a structural unit derived from furfuryl (meth)acrylate of the following Formula (1):

Chemical Formula 1

Formula (1)

in the Formula (1), $R^1$ is a hydrogen atom or a methyl group, and $R^2$ is a group represented by the following Formula (1-1) or the following Formula (1-2):

Chemical Formula 2

Formula (1-1)

Formula (1-2)

in the Formula (1-1) and the Formula (1-2), $R^3$ is an alkylene group having 1 to 3 carbon atoms.

6. The method according to claim 3, wherein the fluorescent dye is a xanthene-based dye.

7. The method according to claim 1, wherein the protein detection reagent has a quinoline structure.

8. The method according to claim 7, wherein the protein detection reagent is bicinchoninic acid.

9. The method according to claim 1, wherein the protein adsorbent has a structural unit derived from furfuryl (meth)acrylate of the following Formula (1):

Chemical Formula 1

Formula (1)

in the Formula (1), $R^1$ is a hydrogen atom or a methyl group, and $R^2$ is a group represented by the following Formula (1-1) or the following Formula (1-2):

Chemical Formula 2

Formula (1-1)

Formula (1-2)

in the Formula (1-1) and the Formula (1-2), $R^3$ is an alkylene group having 1 to 3 carbon atoms.

10. The method according to claim 1, wherein the fluorescent dye is a xanthene-based dye.

11. A method for evaluating a coating state of a protein adsorbent or an adsorption state of a protein, the method comprising:

irradiating a first substrate with light to detect a first color development state of the first substrate, wherein the first substrate comprises a first coating layer and a polymer substrate, wherein the first coating layer comprises a protein adsorbent and a fluorescent dye, and wherein the first coating layer is formed on at least one surface of the polymer substrate;

irradiating a second substrate with light to detect a second color development state of the second substrate, wherein the second substrate comprises the first coating layer, the polymer substrate, and a second coating layer comprising a protein detection reagent, and wherein the first coating layer and the second coating layer are sequentially formed on at least one surface of the polymer substrate, respectively;

irradiating a third substrate with light to detect a third color development state of the third substrate, wherein the third substrate comprises the first coating layer, the polymer substrate, and a sample comprising a protein, wherein the first coating layer and the sample are sequentially formed on at least one surface of the polymer substrate, respectively;

irradiating a fourth substrate with light to detect a fourth color development state of the fourth substrate, wherein the fourth substrate comprises the first coating layer, the polymer substrate, the sample comprising the protein, and the protein detection reagent, wherein the first coating layer, the sample, and the protein detection reagent are sequentially formed on at least one surface of the polymer substrate, respectively; and comparing the fourth color development state with the first, second, and third color development states to evaluate the coating state of the protein adsorbent or the adsorption state of the protein.

12. The method according to claim 11, wherein in a case where light absorption of the fluorescent dye is suppressed in the fourth color development state as compared with the first, second, or third color development states, it is evaluated that the protein is adsorbed on the polymer substrate or the protein adsorbent is coated on the polymer substrate.

13. The method according to claim 11, wherein one of more of the following is true:
the protein detection reagent has a quinoline structure; and
the fluorescent dye is a xanthene-based dye.

14. The method according to claim 13, wherein the protein detection reagent is bicinchoninic acid.

15. The method according to claim 11, wherein the protein adsorbent has a structural unit derived from furfuryl (meth) acrylate of the following Formula (1):

Chemical Formula 1

Formula (1)

in the Formula (1), $R^1$ is a hydrogen atom or a methyl group, and $R^2$ is a group represented by the following Formula (1-1) or the following Formula (1-2):

Chemical Formula 2

Formula (1-1)

Formula (1-2)

in the Formula (1-1) and the Formula (1-2), $R^3$ is an alkylene group having 1 to 3 carbon atoms.

* * * * *